(12) United States Patent
Ohmes

(10) Patent No.: US 6,254,386 B1
(45) Date of Patent: Jul. 3, 2001

(54) DENTAL MIRROR WITH DISPOSABLE TRANSPARENT COVER

(75) Inventor: Jay Ohmes, St. Charles, MO (US)

(73) Assignee: Erik Wendel, Lee's Summit, MO (US)

( * ) Notice: Subject to any disclaimer, the term of this patent is extended or adjusted under 35 U.S.C. 154(b) by 0 days.

(21) Appl. No.: 09/549,120

(22) Filed: Apr. 13, 2000

(51) Int. Cl.[7] ........................................ A61B 1/24
(52) U.S. Cl. ................................................. 433/30
(58) Field of Search ............................ 433/30, 31, 116; 359/511; 206/820

(56) References Cited

U.S. PATENT DOCUMENTS

| | | | |
|---|---|---|---|
| 516,092 | * | 3/1894 | Hills ........................................ 433/30 |
| 2,659,272 | * | 11/1953 | Goldmann ............................... 433/30 |
| 4,394,904 | * | 7/1983 | Larimore ................................ 206/820 |
| 4,511,329 | * | 4/1985 | Diamond ................................. 433/31 |
| 4,713,002 | * | 12/1987 | Presser et al. .......................... 433/30 |
| 5,409,753 | * | 4/1995 | Perez ..................................... 206/820 |
| 5,636,984 | * | 6/1997 | Gomes .................................... 433/30 |
| 5,894,923 | * | 4/1999 | Hamstra et al. ....................... 206/820 |

\* cited by examiner

Primary Examiner—John J. Wilson
(74) Attorney, Agent, or Firm—Shook, Hardy & Bacon L.L.P.

(57) ABSTRACT

A dental instrument in the form of a dental mirror has a removable and disposable transparent cover positioned on the reflective surface of the mirror. The removable transparent cover is preferably formed of flexible plastic. In one embodiment, the protective cover has an adhesive coating for adhering the cover to the reflective surface of the mirror. In another embodiment, the transparent cover adheres to the reflective surface by static cling. In a preferred aspect of one embodiment of the invention, a plurality of transparent covers are provided on a laminate or strip that may be folded or rolled for easy-storage in a container or dispenser.

8 Claims, 1 Drawing Sheet

DENTAL MIRROR WITH DISPOSABLE TRANSPARENT COVER

BACKGROUND OF THE INVENTION

1. Field of the Invention

The present invention is generally directed to a dental instrument. More particularly, the present invention is generally directed to a removable and disposable transparent plastic cover for covering, and thereby protecting, a portable dental mirror inserted into a dental patient's mouth during a dental process, such as an abrasive dental treatment, as is used for cleaning and/or structural work on teeth.

2. Description of the Related Art

Dental mirrors are well known. Dental mirrors typically consist of a handle having a head at one end thereof. A small mirror is mounted to the head of the dental instrument. Dental healthcare professionals utilize the dental mirrors when performing dental applications and treatments, such as teeth-cleaning processes, by placing the head of the dental mirror (and thus the mirror) into the mouth of the patient, thereby permitting the dental professional to view portions of the patient's mouth, teeth, and/or gums that would otherwise be visually inaccessible. In this regard, at least a portion of the handle of a conventional dental mirror is often angled to facilitate the type of visual access that is desired under such circumstances.

One conventional and increasingly popular type of teeth cleaning technique and dental restructuring utilizes an abrasive process. In particular, particulate laden liquid (or high pressure air) is streamed into a dental patient's mouth and, particularly, in contact with the patient's teeth. The particulate, when applied with force against the patient's teeth, has the effect of removing stains or tooth structure, thereby providing a very effective process for cleaning the teeth of the patient. Throughout this document, reference to dental treatment, teeth cleaning treatment and the like shall mean any abrasive dental treatment in which particulate is utilized to clean and/or reshape the teeth.

A problem encountered when utilizing an abrasive dental process of the type described, however, is that the reflective surface of a conventional dental mirror, which is typically used in conjunction with such an abrasive dental process, is itself scratched, thus rendering them useless. Accordingly, such mirrors have to be frequently replaced when they are utilized in conjunction with abrasive dental processes.

Accordingly, the need exists for a dental mirror, including a device for protecting the mirror, which may be utilized in conjunction with abrasive dental processes, without the need to discard the mirror after repeated use. More particularly, the need exists for a device for protecting the reflective surface of a dental mirror when it is utilized in an abrasive dental process. The present invention meets this need while overcoming past problems of the prior art.

SUMMARY OF THE INVENTION

A portable, hand-held dental instrument of the present invention has a handle having a first and a second outer end. A head, for holding a small mirror having a reflective surface, is fixedly positioned within the head. Such dental instruments are well known in the prior art and are conventionally used by dental professionals. In particular, the head portion of the dental instrument, including the mirror, is inserted into the mouth of a dental patient and positioned so as to allow a dental professional to view, via the reflective surface of the mirror, portions of the mouth, teeth, gums, tongue, etc. that would otherwise be difficult or impossible to access visually.

In accordance with an aspect of the invention, a transparent cover is provided and is releasably positioned on the reflective surface of the mirror. Preferably, the transparent cover is dimensioned in shape to precisely cover the reflective surface of the mirror. The transparent cover is preferably formed of flexible plastic material, although may be rigid or semi-rigid. Additionally, in one embodiment of the invention, the transparent, protective cover has an adhesive coating on one side surface thereof. Prior to placement on the reflective surface of the mirror, the protective cover is provided with a sheet, or backing, to prevent exposure of the adhesive. Upon removal of the protective cover from the backing sheet, the exposed adhesive is used to adhere the protective cover to the surface of the mirror.

In a second embodiment, there is no adhesive coating on the transparent, protective cover. Rather, the transparent, protective cover adheres, or clings, to the mirror by static.

In a particularly preferred embodiment of the invention, a plurality of transparent, protective mirror covers are placed on a flexible laminate, or strip. In the embodiment in which the protective cover has an adhesive coating, the strip serves as the backing sheet for preventing exposure of the adhesive until such time as the cover is to be used. In the embodiment in which the adhesive is not utilized, the protective cover is defined by a line of weakness, or perforation, such that the protective cover may be torn from the strip along the line of weakness or perforation. A flexible strip may be folded upon itself, or formed into a roll, in either case making the flexible strip with individual covers thereon easily storable in a container or dispenser.

In use, a transparent protective cover is removed from the strip and placed over, and on, the reflective surface of the mirror. The mirror may then be utilized in a dental application, such as an abrasive teeth-cleaning or dental restructuring process. During an abrasive dental process, a stream of particulate laden liquid or air is applied to the teeth of a patient. To clean areas of the teeth that are visually inaccessible, the mirror of the present invention, having the protective cover thereon, may be inserted into the patient's mouth to provide a reflective view, as needed. In such instances, it is highly probable that particulate utilized in the abrasive dental treatment process will impact on the protective cover, thereby causing abrasions on the cover. At some point, and after a certain duration of use, depending upon the circumstances, the transparent protective cover will have more abrasions on it than are desirable, thereby inhibiting a clear, reflective view with the mirror. At such a time, the dental professional may remove the dental mirror of the invention from the patient's mouth, and remove the damaged transparent protective cover by peeling it away from the mirror. A second protective cover may then be put in place of the damaged one, and the teeth cleaning process may be continued. Similarly, at the end of the teeth cleaning treatment, the protective cover may be discarded (even if it was not significantly damaged) and the instrument may be sterilized in a conventional fashion. It should also be understood that the dental instrument may be sterilized with the protective cover in place, although the disposability of the present invention makes it particularly useful for disposal upon completion of an abrasive dental process.

BRIEF DESCRIPTION OF THE DRAWINGS

The objects and features of the invention noted above are explained in more detail with reference to the drawings, in which like reference numerals denote like elements, and in which.

DETAILED DESCRIPTION OF THE INVENTION

Figure 1:
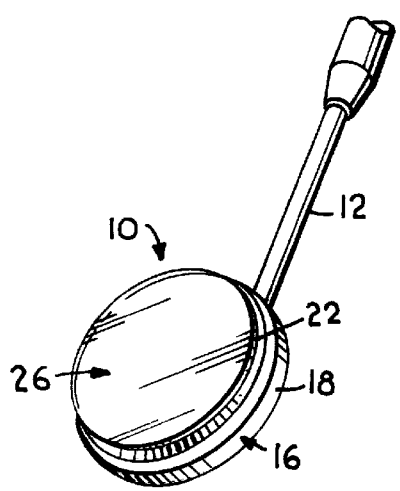
FIG. 1 is a perspective view of a dental instrument and, particularly, a dental mirror having a removable protective cover of the present invention.
Figure 2:
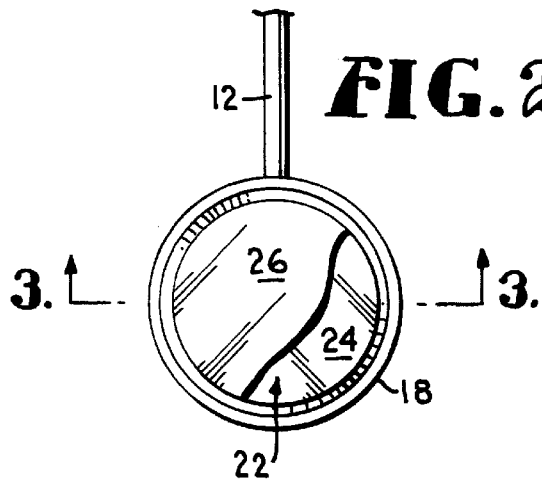
FIG. 2 is a top plan view of the dental mirror of the present invention.
Figure 3:
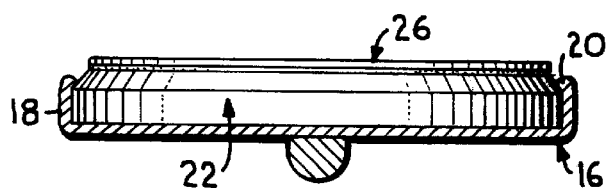
FIG. 3 is an elevational view of the dental mirror of the present invention, taken along lines 3—3 of FIG. 2.

With reference initially to FIGS. 1–3, a dental instrument of the present invention and, particularly, a dental mirror of the present invention, is denoted generally be reference numeral 10. The dental mirror 10 has a handle 12 having first and second outer ends. In particular, a first end, denoted by reference numeral 14 of the handle 12 has a head portion 16 affixed thereto. The second end (not shown), is positioned at the opposite end of handle 12. The head portion 16, which may be of any desirable configuration, is typically round and is of a dimension which permits the head portion 16 to be easily inserted into the mouth of a dental patient. As illustrated best in FIG. 3, the head portion 16 has an annular flange 18, terminating in a small lip 20, thereby providing a holder for a mirror, denoted generally by reference numeral 22. Mirror 22 has a reflective upper surface 24. The foregoing described instrument 10 is a conventional dental instrument found in the prior art, and with which dental professionals will be readily familiar.

In accordance with an aspect of the present invention, the dental instrument 10 of the present invention is transparent and has a protective cover 26. In particular, transparent cover 26 is preferably formed of a flexible plastic, although may be rigid or semi-rigid and, in a most preferred embodiment, is formed of top coated highly plasticsized clear cling vinyl film. The transparent cover 26 is sized and dimension to precisely fit on the reflective surface 24 of mirror 22.

Figure 4:
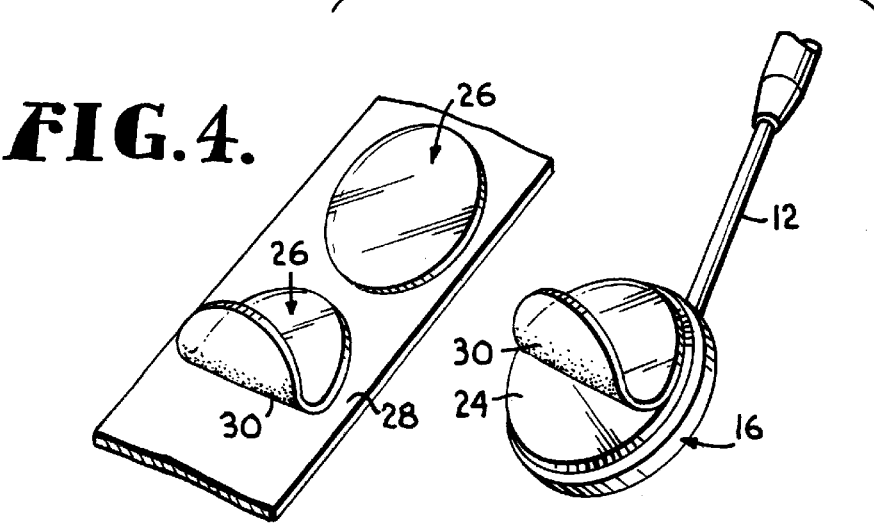
FIG. 4 is a perspective view of a strip releasably holding a plurality of dental mirror covers in accordance with the present invention, and an illustration of use of a dental mirror cover of the present invention on a dental mirror of the present invention.

With reference now to FIG. 4, the transparent cover 26 of the present invention and, particularly, a device for holding a plurality of such covers 26 is illustrated and described, along with an illustration of the preferred use of the cover 26.

A strip or laminate 28, which is preferably flexible, paper-like, film-like, or of plastic strip is provided. A plurality of transparent covers 26 of the present invention are positioned on the strip 28. Due to the preferably flexible nature of strip 28, the strip is adapted for folding upon itself, or rolling into a roll, thereby permitting the strip 28, with a multitude of covers 26 thereon, to be readily positioned into a container or dispenser.

In accordance with one embodiment of the present invention, each transparent cover 26 has a rear surface having an adhesive thereon, as indicated by reference numeral 30. As further illustrated in FIG. 4, a transparent cover 26 may be peeled from the strip 28, and adhesively secured to the reflective surface 24 of the mirror 22 of dental instrument 10. It should be understood and appreciated that each transparent cover 26 may be individually packaged and thus not presented on the strip 28. However, utilization of the strip 28 is the preferred form of the invention.

In an alternate embodiment of the present invention, the transparent covers 26 do not have an adhesive backing, but are rather adhered to the reflective surface 24 of mirror 22 by static cling. While, in such an embodiment, the covers 26 may be provided loosely, in one embodiment they are presented in a strip of the same type of plastic material from which the cover 26 is made, and are separable from the strip by a line of weakness or a line of weakness (e.g., a perforated line).

In use, a protective, transparent cover 26 is removed from its backing sheet, in the event one is provided, such as backing sheet (or strip) 28. Transparent, cover sheet 26 is then placed on the reflective surface 24 of mirror 22 of the dental instrument 10. The instrument is then usable in a conventional fashion. In particular, when the transparent cover 26 that is placed on the mirror 22 is worn, it may be removed by simply peeling the cover off of the reflective surface 24 of mirror 22.

Particularly, the dental instrument 10 in combination with the protective cover 26 is particularly useful in abrasive dental techniques. In such instances, an abrasive dental treatment apparatus forces a particulate laden liquid (or airstream) into the teeth of a dental patient. The particulate serves as an abrasive material, thereby cleaning the teeth of stain or restructuring the surface of the teeth. During such an abrasive dental treatment process, the dental instrument 10 may be utilized to permit the dental professional to visually view, reflectively, areas that would otherwise be difficult or impossible to view. During the abrasive dental process, the particulate is likely to impact upon the transparent protective cover 26, resulting in its damage over time. When the protective cover 26 becomes worn to the point that the dental professional desires to replace it, the dental instrument 10 is simply removed from the patient's mouth, the worn transparent protective cover 26 is removed from the reflective surface 24 of the mirror 22, and a second, new transparent cover 26 is located in its place. Following completion of the abrasive dental process, the transparent cover 26 then in place on the mirror may be removed and discarded (which is preferred) or, alternatively, in some instances, the entire instrument 10 with transparent cover 26 may be sterilized for future use.

In summary, the dental instrument of the present invention provides a dental mirror in combination with a removable transparent cover, the transparent cover 26 of the present invention itself, and the strip of a plurality of transparent covers 26 all providing much needed improvements in the dental industry. Particularly, with the advent of the present invention, conventional dental mirrors may be utilized in an abrasive dental treatment processes without marring the reflective surface of the mirror.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

What is claimed is:

1. A dental instrument comprising:
    a handle having first and second outer ends;
    a mirror disposed at said first outer end of said handle; and
    a removable, transparent cover positioned on said mirror,
        wherein said transparent cover is releasably retained on said mirror by at least one of an adhesive on a surface of said mirror and static cling.

2. The dental instrument as set forth in claim 1, said removable transparent cover comprised of plastic.

3. The dental instrument as set forth in claim 1, said mirror having a reflective surface defined by a periphery, said cover sized to precisely cover said reflective surface of said mirror.

4. The dental instrument as set forth in claim 3, wherein said mirror is round.

5. The dental instrument as set forth in claim 1, wherein said cover is for protecting said mirror when said mirror is utilized in an abrasive dental process.

6. A device in combination with a small, portable mirror, having a reflective surface, when said mirror is used in a dental application, said device comprising:

a transparent cover shaped and dimensioned to precisely cover said reflective surface of said mirror, said transparent cover having a first side and a second side, said first side having adhesive thereon for releasably adhering to said mirror.

7. The device as set forth in claim 6, further comprising:

a peel-away sheet covering said adhesive, said peel-away sheet being removed prior to said adherence of said cover with said mirror.

8. A method comprising:

providing an abrasive dental treatment apparatus;

providing a portable, dental mirror for insertion into the mouth of a patient;

providing a transparent cover;

releasably positioning said transparent cover on said mirror by at least one of an adhesive and static cling;

using said abrasive dental treatment apparatus on the teeth of said patient; and when a determination is made that said transparent cover requires replacement due to abrasion resulting from said abrasive dental treatment, then removing said transparent cover and positioning a second, new transparent cover on said mirror.

\* \* \* \* \*